United States Patent
Nakamura

(10) Patent No.: US 10,359,393 B2
(45) Date of Patent: Jul. 23, 2019

(54) GAS SENSOR

(71) Applicant: DENSO CORPORATION, Kariya, Aichi-pref. (JP)

(72) Inventor: Masatake Nakamura, Kariya (JP)

(73) Assignee: DENSO CORPORATION, Kariya (JP)

(*) Notice: Subject to any disclaimer, the term of this patent is extended or adjusted under 35 U.S.C. 154(b) by 268 days.

(21) Appl. No.: 15/120,588

(22) PCT Filed: Apr. 23, 2015

(86) PCT No.: PCT/JP2015/062339
§ 371 (c)(1),
(2) Date: Aug. 22, 2016

(87) PCT Pub. No.: WO2015/163393
PCT Pub. Date: Oct. 29, 2015

(65) Prior Publication Data
US 2017/0010235 A1    Jan. 12, 2017

(30) Foreign Application Priority Data
Apr. 25, 2014 (JP) .................................. 2014-090919

(51) Int. Cl.
G01N 27/407 (2006.01)
G01N 27/416 (2006.01)
G01N 27/409 (2006.01)

(52) U.S. Cl.
CPC ....... *G01N 27/409* (2013.01); *G01N 27/4077* (2013.01)

(58) Field of Classification Search
CPC .. G01N 27/406; G01N 27/407; G01N 27/416; G01N 27/409; G01N 27/4077
See application file for complete search history.

(56) References Cited

U.S. PATENT DOCUMENTS

| 4,019,974 A * | 4/1977 | Weyl ................. G01N 27/4062 204/428 |
| 5,966,078 A * | 10/1999 | Tanguay ................ G08B 17/10 340/628 |
| 2006/0065541 A1* | 3/2006 | Nishio ................ G01N 27/4077 205/427 |
| 2014/0190829 A1 | 7/2014 | Tabuchi et al. |

FOREIGN PATENT DOCUMENTS

| JP | S55-017164 | 2/1980 |
| JP | H06-235714 | 8/1994 |
| JP | H11-190715 | 7/1999 |
| JP | 2013-167625 | 8/2013 |

* cited by examiner

*Primary Examiner* — Susan D Leong
(74) *Attorney, Agent, or Firm* — Nixon & Vanderhye PC

(57) ABSTRACT

A gas sensor includes a housing, an insulator, an inner cover, and an outer cover. An inner peripheral hole of the housing includes a rear end side hole and a front end side hole portion and a rear end side hole portion. A step portion which is formed in a slant shape is provided at a boundary between the front end side hole portion and the rear end side hole portion. The inner cover has a large-diameter portion which faces the step portion. The insulator has a flange which holds the large-diameter portion between itself and the step portion. A burr is formed on the surface of the large-diameter portion. The burr faces the surface of the step portion. This avoids inclination of the cover relative to the inner peripheral hole of the housing and obviates the risk of damage to or breakage of a device body.

8 Claims, 8 Drawing Sheets

FIG.7
(a)
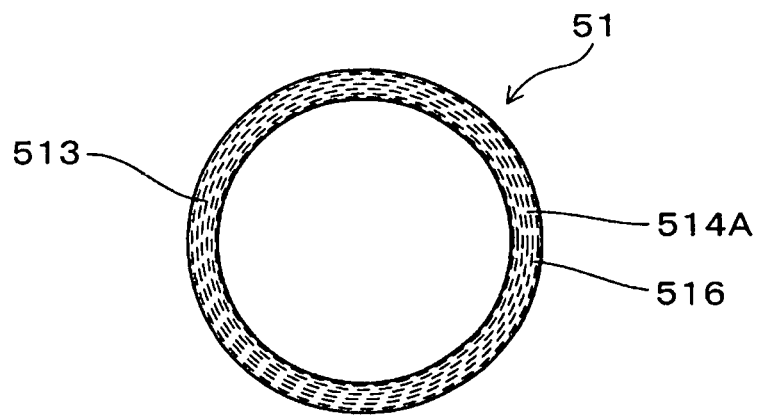
(b)
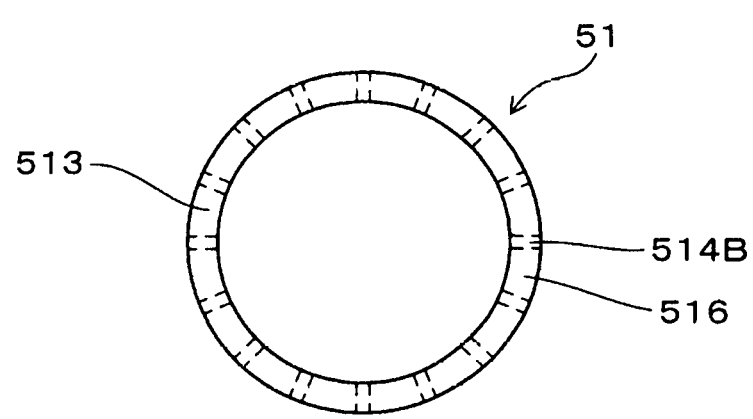
(c)
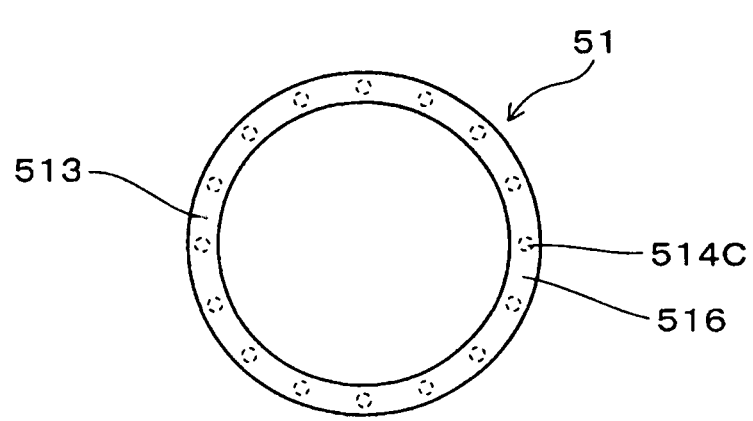

FIG.9
(a)
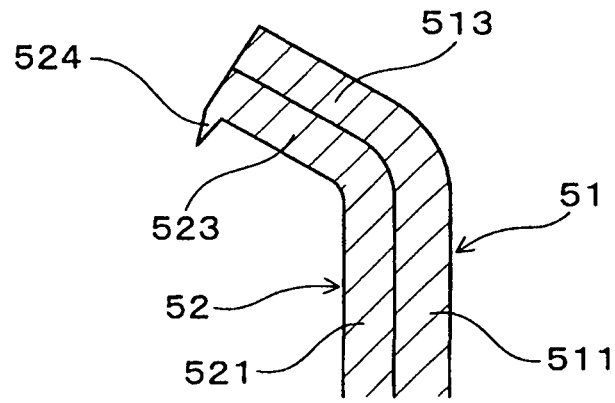
(b)
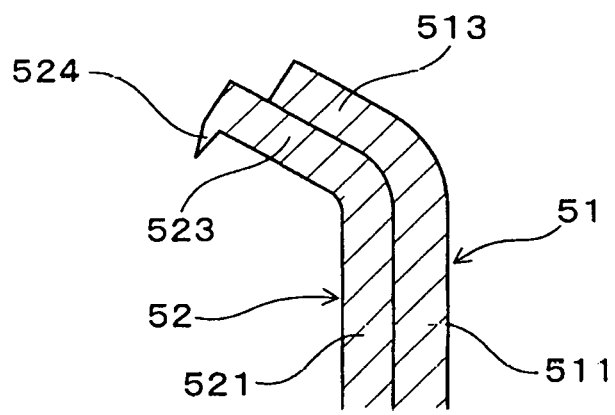
(c)
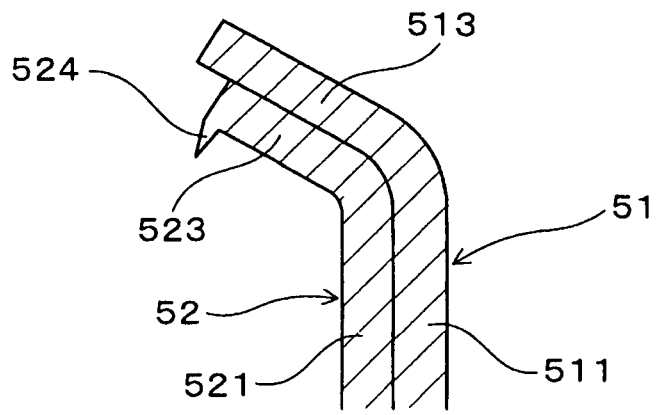

GAS SENSOR

This application is the U.S. national phase of International Application No. PCT/JP2015/062339 filed 23 Apr. 2015 which designated the U.S. and claims priority to JP Patent Application No. 2014-090919 filed 25 Apr. 2014, the entire contents of each of which are hereby incorporated by reference.

TECHNICAL FIELD

The present invention generally relates to a gas sensor in which a cover is held between a device body and an inner peripheral hole of a housing.

BACKGROUND ART

A gas sensor which measures the concentration of oxygen holds a cover which covers a portion of a gas sensing device between the gas sensing device or a device body into which the gas sensing device is inserted and an inner peripheral hole of a housing. The exhaust gas is admitted to a device portion of the gas sensing device through holes of the cover. The device portion measures the concentration of oxygen contained in the exhaust gas.

For instance, Japanese Patent First Publication No. 2013-117521 discloses a gas sensor having a device body which is of a cylindrical shape with a bottom and equipped with a flange extending outwardly in a radial direction. The device body is inserted into a tubular metal shell which has a seating surface facing the flange. An annular metallic portion is disposed between the flange of the device body and the seating surface of the metal shell to avoid a positional shift of the metallic portion in the radial direction. The metal shell corresponds to a housing. The metallic portion corresponds to a cover.

SUMMARY OF THE INVENTION

Problem to be Solved by the Invention

The insertion of the cover into the inner peripheral hole of the housing requires an air gap between the inner peripheral hole and the cover. The air gap, however, undesirably facilitates inclination of a central axis of the cover relative to the central axis of the device body and the housing in the insertion direction when the cover is retained between the device body and the inner peripheral hole of the housing. The load, as created by retaining the cover, is exerted on the device body, which leads to the risk of damage to or breakage of the device body.

The present invention was made against such a background to provide a gas sensor which is capable of avoiding inclination of a cover relative to an inner peripheral hole of a housing which may lead to damage to or breakage of a device body.

Means for Solving the Problem

One embodiment of the invention is a gas sensor which comprises: (a) a tubular housing; (b) a device body which is inserted into an inner peripheral hole of the housing, the device body being a gas sensing device or a member into which the gas sensing device is inserted; and (c) a cover which covers a portion of the gas sensing device and is held between the inner peripheral hole of the housing and the device body. The inner peripheral hole of the housing includes a front end side hole portion, a rear end side hole portion, and a step portion. The front end side hole portion is located on a front end side of the device body. The rear end side hole portion is located closer to a rear end side than the front end side hole portion is and has a diameter greater than that of the front end side hole portion. The step portion is formed in a vertical or slant shape at a boundary between the rear end side hole portion and the front end side hole portion. The cover includes a tubular portion inserted into the front end side hole portion and a large-diameter portion which has a diameter greater than the tubular portion and which faces the step portion. The device body has a flange which protrudes from an outer circumference thereof and holds the large-diameter portion between itself and the step portion. At least one of surfaces of the step portion and the large-diameter portion which face each other has a convex portion protruding toward the other surface.

Beneficial Effect of the Invention

In the above gas sensor, the convex portion protruding toward the other surface is provided on at least one of the surfaces of the step portion and the large-diameter portion which face each other.

The assembling of the gas sensor is achieved by inserting the cover into the inner peripheral hole of the housing and also inserting the device body into an inner peripheral side of the inner cover. Specifically, a tubular portion of the cover is inserted into the front end side hole portion of the inner peripheral hole of the housing, so that the large-diameter portion of the cover faces the step portion of the inner peripheral hole of the housing, and the flange of the device body also faces the large-diameter portion of the cover.

When load which holds the cover is applied to between the inner peripheral hole of the housing and the device body, the convex portion formed on at least one of the step portion and the large-diameter portion is elastically or plastically deformed and bites into the other. This causes the cover to be kept inserted parallel into the inner peripheral hole of the housing, thereby avoiding inclination of the center axis of the cover relative to the center axis of the inner peripheral hole of the housing.

The exertion of the load on between the inner peripheral hole of the housing and the device body will result in elastic and plastic deformation of the convex portion on the at least one of the step portion and the large-diameter portion, thereby reducing a reactive force acting on the device body. The elastic or plastic deformation of the convex portion reduces the reactive force which the device body undergoes and corrects the inclination of the cover to avoid undesirable interference of the large-diameter portion of the cover with the device body.

The gas sensor 1 is, therefore, capable of avoiding the inclination of the cover relative to the inner peripheral hole of the housing to obviate the risk of damage to or breakage of the device body.

BRIEF DESCRIPTION OF THE DRAWINGS

FIG. 7(a) is an illustration of a plurality of protrusions on a large-diameter portion of an inner cover, as viewed from a center axis of the inner cover, in an embodiment and shows the protrusions which are formed in a radial direction;

FIG. 7(b) is an illustration of a plurality of protrusions on a large-diameter portion of an inner cover, as viewed from a center axis of the inner cover, in an embodiment and shows the protrusions which are formed in a circumferential direction;

FIG. 7(c) is an illustration of a plurality of protrusions on a large-diameter portion of an inner cover, as viewed from a center axis of the inner cover, in an embodiment and shows the protrusions which are formed in a circumferential direction;

FIGS. 9(a), 9(b), and 9(c) are explanatory enlarged sectional views which illustrate around large-diameter portions formed on an inner cover and an outer cover according to an embodiment.

EMBODIMENT FOR CARRYING OUT THE INVENTION

A preferred embodiment of the above described gas sensor will be described below.

In the above gas sensor, the above described large-diameter portion is formed in a slant shape so that the diameter of a rear portion of the above tubular portion increases toward a rear end side thereof. The above step portion is formed in a slant shape so that the diameter increases toward a rear end side thereof. The above convex portion may be formed on at least one of a surface of a stop end portion of the step or a surface of a rear end portion of the large-diameter portion.

In this case, it is easy to align the center with the housing when the surface of the slant step faces the surface of the slant large-diameter portion.

The above convex portion may be formed to protrude from the surface of the above large-diameter portion.

This facilitates digging in of the convex portion.

The above convex portion may be formed to protrude from a surface of the large-diameter portion of the cover when the cover is machined.

In this case, burrs which are inevitably formed on a machined portion of the cover when the cover is subjected to cutting work, press work, spinning work, or drawing work may be used as the convex portion. Particularly, burrs formed when material of the cover is cut may be used as the convex portion.

The convex portion may be formed to protrude from the surface of the step portion.

In this case, it is easy to achieve the biting in of the convex portion.

The convex portion may be implemented by a plurality of protrusions provided on at least one of the step portion and the large-diameter portion.

In this case, the plurality of protrusions may be formed on the at least one of the step portion and the large-diameter portion by means of various types of surface machining. The plurality of protrusions may be formed on the surface of the step portion or the large-diameter portion when the housing or the cover is machined.

EMBODIMENT

An embodiment of a gas sensor will be described below with reference to the drawings.

Figure 1:
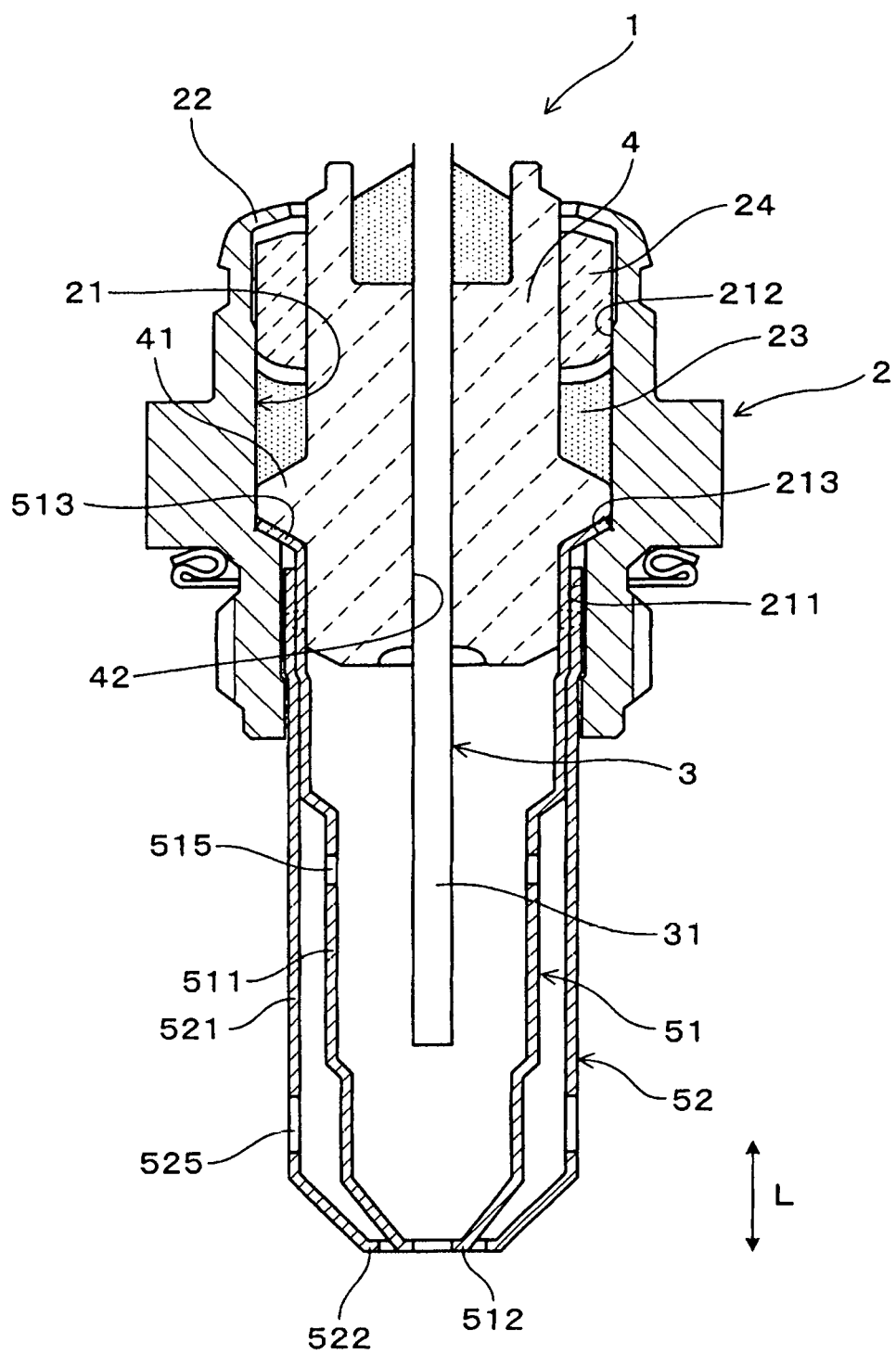
FIG. 1 is a sectional explanatory view which illustrates a gas sensor according to an embodiment.

The gas sensor 1 of this embodiment, as illustrated in FIG. 1, includes a tubular housing 2, an insulator 4, an inner cover 51, and an outer cover 52. The insulator 4 is inserted into an inner peripheral hole (also called an inner chamber) of the housing 2 and into which a gas sensing device 3 is inserted. The insulator 4 serves as a device body. The inner cover 51 and the outer cover 52 cover a portion of the gas sensing device 3 and are retained between the inner peripheral hole 21 of the housing 2 and the insulator 4. The inner peripheral hole 21 of the housing 2 includes a front end side hole portion 211, a rear end side hole portion 212, and a step portion 213. The front end side hole portion 211 is located on a front end side of the insulator 4. The rear end side hole portion 212 is located closer to the rear end side than the front end side hole portion 211 is and has a diameter greater than that of the front end side hole portion 211. The step portion 213 (which will also be referred to as an inner shoulder below) is formed in a slant shape at a boundary between the rear end side hole portion 212 and the front end side hole portion 211.

Figure 2:
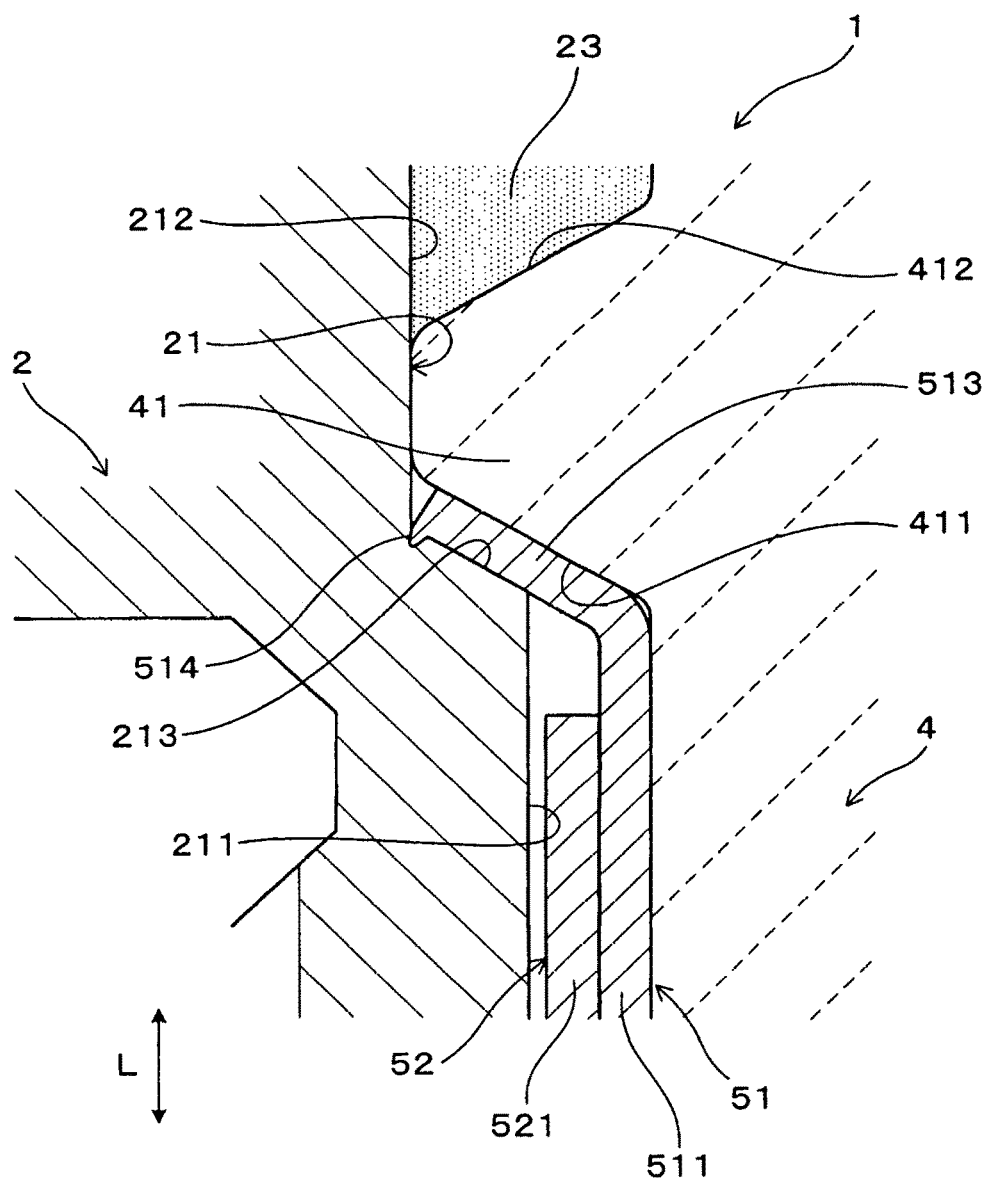
FIG. 2 is an explanatory sectional enlarged view which illustrates around a large-diameter portion of an inner cover of a gas sensor according to an embodiment.

The inner cover 5, as illustrated in FIG. 2, includes a tubular portion 511 inserted into the front end side hole portion 211 and a large-diameter portion 513 which is greater in diameter than the tubular portion 511 and faces the step portion 213. The insulator 4 has a flange 41 which protrudes from an outer periphery thereof and holds the large-diameter portion 513 between itself and the step portion 213. The large-diameter portion 513 has formed on a surface thereof a burr 514 which protrudes as a convex portion toward the surface of the step portion 213.

The gas sensor 1 of this embodiment will be described in detail with reference to FIGS. 1 to 7.

The gas sensor 1 is mounted in, for example, an exhaust pipe connecting with an internal combustion engine to measure the concentration of oxygen contained in exhaust gas emitted from the internal combustion engine. The inner cover 51 and the outer cover 52 of the gas sensor 1 are disposed inside the exhaust pipe.

The inner cover 51 and the outer cover 52, as illustrated in FIG. 1, have formed therein through-holes 515 and 521 for bringing the exhaust gas as measured gas to a measuring portion 31 (i.e., a sensing portion) of the gas sensing device 3 disposed inside the inner cover 51. The inner cover 51 is arranged inside an inner periphery of the outer cover 52 and overlaps it. The location of the through-holes 525 of the outer cover 52 in an axial direction L is different from that of the through hole 515 of the inner cover 51 in the axial direction L.

The axial direction L is a direction in which the inner peripheral hole 21 of the housing 2 is formed. The center axis is a virtual line passing through the center of the inner peripheral hole 21 of the housing 2.

The front end side is a side where the inner cover 51 and the outer cover 52 protrude from the housing 2 or where the measuring portion 31 of the gas sensing device 3 protrudes from the insulator 4. The rear end side is an opposite side of the front end side.

The large-diameter portion 513 of this embodiment is, as illustrated in FIG. 1, formed in a slant shape and has a diameter which increase toward the rear end side at the rear end portion of the tubular portion 511 of the inner cover 51. The large-diameter portion 513 is formed as a flange which is bent obliquely from a rear end portion of the tubular portion 511 parallel to the axial direction L. The inner cover 51 and the outer cover 52 are formed in a bottomed tubular shape and have the tubular portions 511 and 521 and bottoms 512 and 522 formed on the front end of the tubular portions 511 and 521. The through-holes 515 and 525 are formed in the tubular portion 511 and 521 and the bottoms 521 and 522.

The insulator 4 has formed in a central portion thereof an insertion hole 42 into which the gas sensing device 3 is inserted. The gas measuring portion 31 of the gas sensing device 3 which measures the concentration of oxygen protrudes from the insulator 4 to the front end side in the axial direction L. The flange 41 of the insulator 4 is formed to protrude to have the whole circumference whose diameter increases. The flange 41 has the front end side surface 411 formed at substantially the same angle of slope as that at which the large-diameter portion 513 is formed.

A rear end side of the tubular portion 511 of the inner cover in the axial direction L and a rear end side portion of the tubular portion 521 of the outer cover 52 in the axial direction L are inserted into and disposed in the front end side hole portion 211 of the inner peripheral hole 21 of the housing 2. The surface of the step portion 213 of the housing 2 is formed in a slant shape to have a diameter which increases toward the rear end side thereof.

Figure 3:
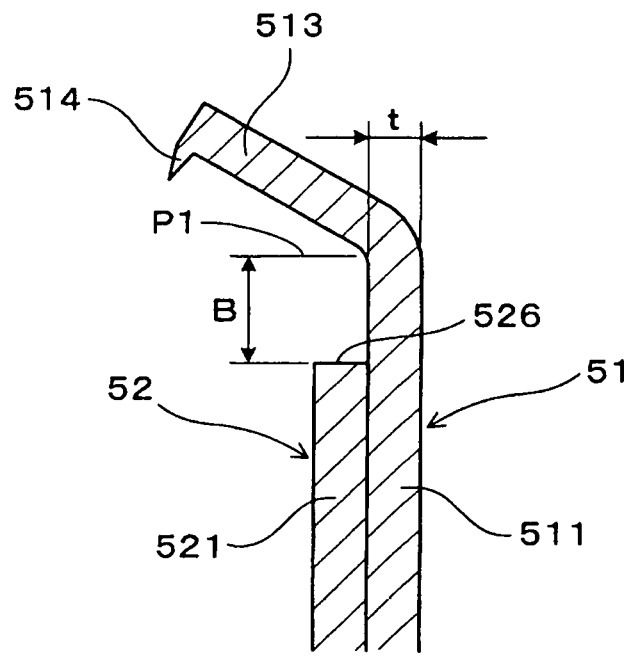
FIG. 3 is an explanatory sectional enlarged view of around a large-diameter portion of an inner cover before being installed in a gas sensor according to an embodiment.

The burr 514 provided on the surface of the large-diameter portion 513 of the inner cover 51 of this embodiment is, as illustrated in FIG. 3, a burr which is formed to have a pointed top protruding from the surface of the large-diameter portion 513 when the inner cover 51 is machined. The burr 514 is formed to protrude from the surface of a rear end portion of the large-diameter portion 513 toward the front end side. The burr 514 may be made by a protrusion formed on an end of a base material of the inner cover 51 when the inner cover 51 is cut out from the base material.

The tubular portion 511 of the inner cover 51 and the tubular portion 521 of the outer cover 52 are, as illustrated in FIG. 1, partially joined together through the weld 6. The weld 6 is formed to bulge from an outer circumference of the outer cover 52 to make contact with the front end side hole portion 211 of the housing 2. The weld 6 is provided to extend along the whole circumference of the tubular portion 511 of the inner cover 51 and the tubular portion 421 of the outer cover 52 in a circumferential direction thereof. The circumferential direction is a direction around the center axis of the inner cover 51 and the outer cover 52 extending parallel to the axial direction L.

Figure 4:
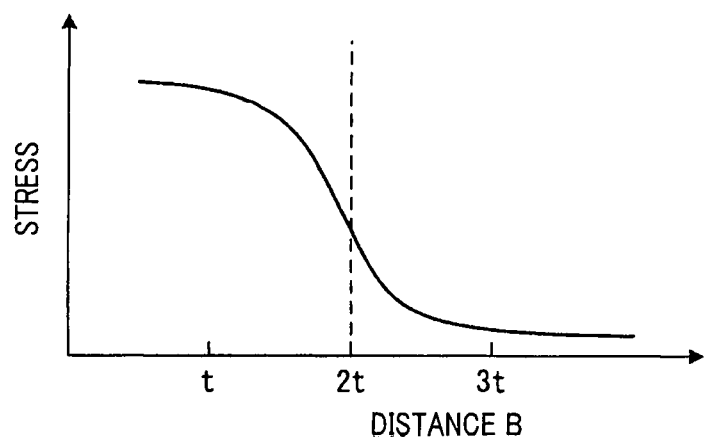
FIG. 4 is a graph which represents a relation of the distance between a bending point of an inside portion of an inner cover and a rear end of an outer cover to a degree of stress produced in an inner cover.

The distance B, as illustrated in FIG. 3, between a bending point P of an inside portion of the large-diameter portion 513 of the inner cover 51 which is bent relative to the tubular portion 521 and the rear end surface 526 of the outer cover 52 is preferably selected to meet a relation of B>t where t is the thickness of the inner cover 51. FIG. 4 is a graph which represents a relation between the distance B and a degree of stress produced in the inner cover 51. FIG. 4 shows that an increase in the distance B will result in a decrease in degree of the stress. The stress is exerted between the rear end portion of the outer cover 52 and the bending point of the inner cover 51. The relation of B>2t will result in a decrease in degree of stress acting on the inner cover 51.

How to assemble the gas sensor 1 of this embodiment and beneficial effects of the gas sensor 1 will be described below.

The assembling of the gas sensor 1 is, as illustrated in FIGS. 1 and 2, achieved by inserting the inner cover 51 and the outer cover 52 into the inner peripheral hole 21 of the housing 2 and also inserting the insulator 4 into an inner peripheral side of the inner cover 51. Specifically, the tubular portion 511 of the inner cover 51 is inserted into the front end side hole portion 211 of the inner peripheral hole 21 of the housing 2, so that the large-diameter portion 513 of the inner cover 51 faces the step portion 213 of the inner peripheral hole 21 of the housing 2, and the front end side surface 411 of the flange 41 of the insulator 4 also faces the rear end surface of the large-diameter portion 513 of the inner cover 51.

In a condition where the inner cover 51, the outer cover 52, and the insulator 4 are inserted into the inner peripheral hole 21 of the housing 2, a gap between the rear end side hole portion 212 of the inner peripheral hole 21 of the housing 2 and the outer periphery of the insulator 4 is filled with insulating powder 23 such as talc. The porcelain insulator 24 is disposed on the rear end side of the insulating powder 23 between the rear end side hole portion 212 and the outer periphery of the insulator 4. The crimping portion 22 formed on the rear end side of the housing 2 is crimped toward the front end side to hold the insulating powder 23 and the porcelain insulator 24 between the rear end side surface 412 of the flange 41 of the insulator 4 and the crimping portion 22 and also retain the large-diameter portion 513 between the step portion 213 of the housing 2 and the front end side surface 411 of the flange 41 of the insulator 4.

In the above crimping, force is produced to press the large-diameter portion 513 against the step portion 213, so that the burr 514 formed on the surface of the rear end portion of the large-diameter portion 513 is elastically or plastically deformed and bites into the surface of the step portion 213. This causes the inner cover 51 and the outer cover 52 to be kept inserted parallel into the inner peripheral hole 21 of the housing 2, thereby avoiding inclination of the center axis of the inner cover 51 and the outer cover 52 relative to the center axis of the inner peripheral hole 21 of the housing 2.

The biting in of the burr 514 avoids rotation of the inner cover 51 and the outer cover 52 about the center axis thereof.

In the above crimping, the burr 514 of the large-diameter portion 513 is elastically or plastically deformed, thereby resulting in a decrease in reactive force to which the insulator 4 is subjected. The elastic or plastic deformation of the burr 514 reduces the reactive force which the insulator 4 undergoes and corrects the inclination of the inner cover 51 and the outer cover 52 to avoid undesirable interference of the large-diameter portion 513 of the inner cover 51 with the insulator 4.

The gas sensor 1 is, therefore, capable of avoiding the misalignment of the inner cover 51 and the outer cover 52 relative to the inner peripheral hole 21 of the housing 2 to obviate the risk of damage to or breakage of the insulator 4.

A convex portion which is formed on at least one of the step portion 213 of the housing 2 and the large-diameter portion 513 of the inner cover 5 is the burr 514 formed when the inner cover 51 is machined, but may alternatively be implemented by a following variety of structures.

Figure 5:
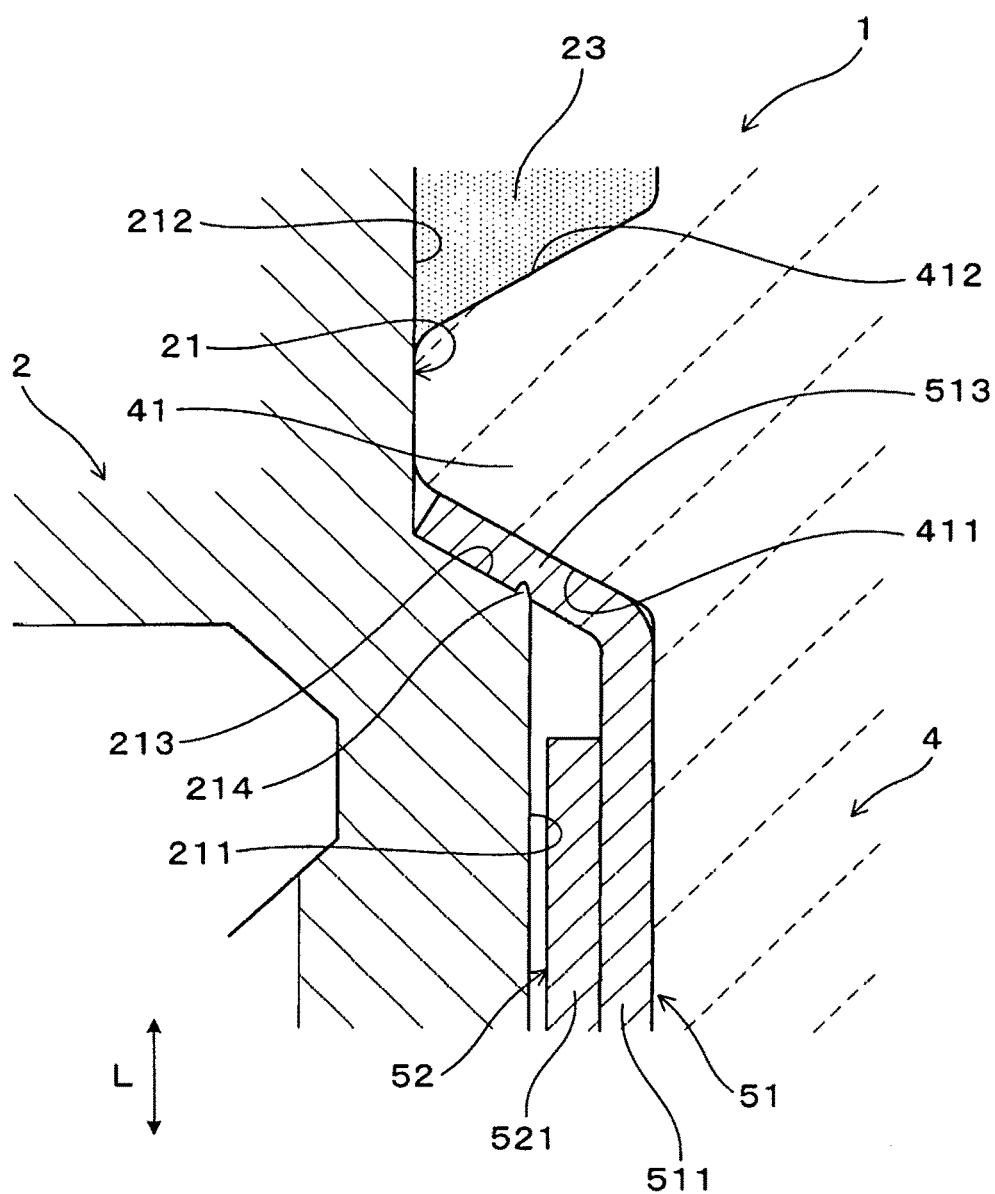
FIG. 5 is an explanatory sectional view which corresponds to FIG. 2 in a case where a convex portion is formed on a step portion of a housing according to an embodiment.

For instance, the convex portion 214 with a pointed head, as illustrated in FIG. 5, may be formed on the surface of a front end portion of the step portion 213 of the housing 2.

Figure 6:
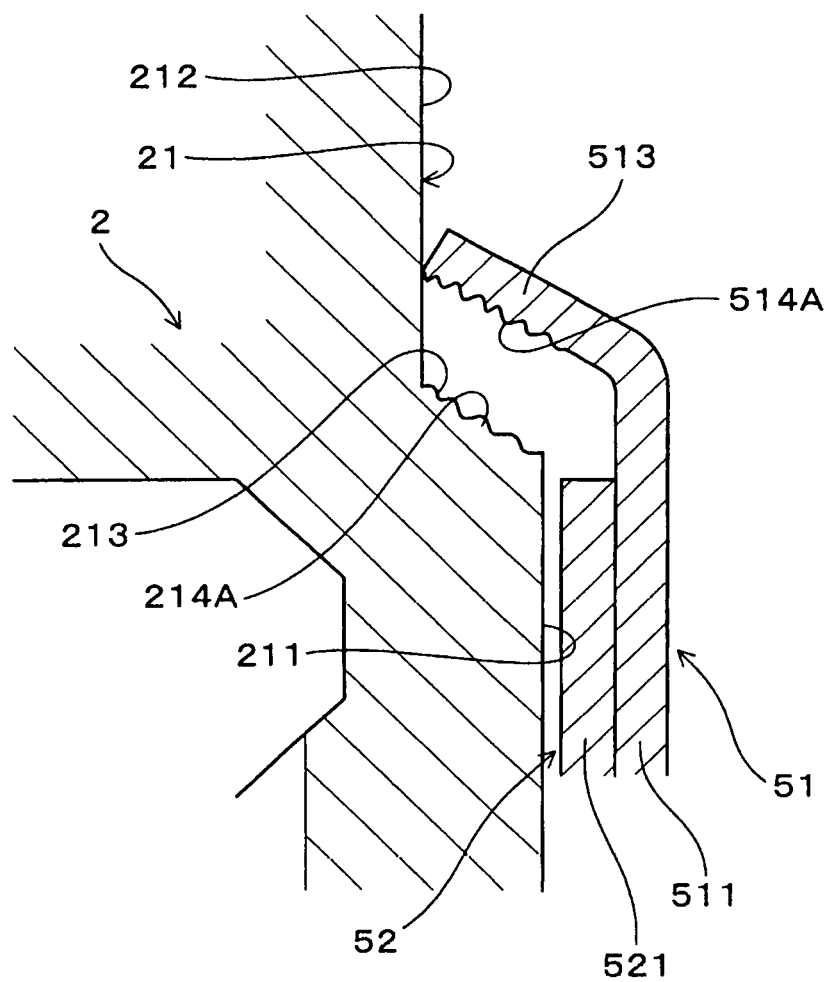
FIG. 6 is an explanatory enlarged sectional view which illustrates around a step portion of another housing and a large-diameter portion of another inner cover in a gas sensor according to an embodiment.

The convex portion may alternatively be, as illustrated in FIG. 6, implemented by a plurality of protrusions 514A formed by machining the large-diameter portion 513 of the inner cover 51. The plurality of protrusions 214A as the convex portion may be formed on the surface of the step portion 213 of the housing 2. In this case, the surface of the step portion 213 of the housing 2 may be machined to make the plurality of protrusions 214A.

Further, the plurality of protrusions 514A may be made to have a configuration, as illustrated in FIGS. 6 and 7(a), where concavities and convexities are formed alternately in the radial direction of the large-diameter portion 513 of the inner cover 51. The plurality of protrusions 514B may be made to have a configuration, as illustrated in FIG. 7(b), where concavities and convexities are formed alternately in the circumferential direction of the large-diameter portion 513 of the inner cover 51. The plurality of protrusions 514C may be made, as illustrated in FIG. 7(c), by a plurality of diple-like protrusions (i.e., a plurality of discrete island protrusions) arrayed in the circumferential direction of the large-diameter portion 513 of the inner cover 51. In the case of FIG. 7(b) or 7(c), the plurality of protrusions may alternatively be formed as the convex portion on the surface of the step portion 213 of the housing 2. In FIGS. 7(a) to 7(c), the convex portion is denoted by a reference number 516.

In the cases of FIGS. 7(a) to 7(c), the above described crimping will cause a high-surface pressure to be exerted on contacts between the protrusions 514B or 514C and the step portion 213 when force is produced which presses the large-diameter portion 513 of the inner cover 51 against the step portion 213 of the housing 2. This minimizes a risk that the inner cover 51 is shifted inwardly or rotated about the center axis due to the exertion of pressure on the inner cover 51.

The device body is the insulator 4, but may alternatively be made by a solid electrolyte body constituting the gas sensing device. The solid electrolyte body is of a tubular shape with a bottom and equipped with a flange similar in shape to the flange 41 of the insulator 4. The solid electrolyte body has a pair of electrodes formed on inner and outer peripheral surfaces thereof for measuring the concentration of oxygen contained in the exhaust gas.

Figure 8:
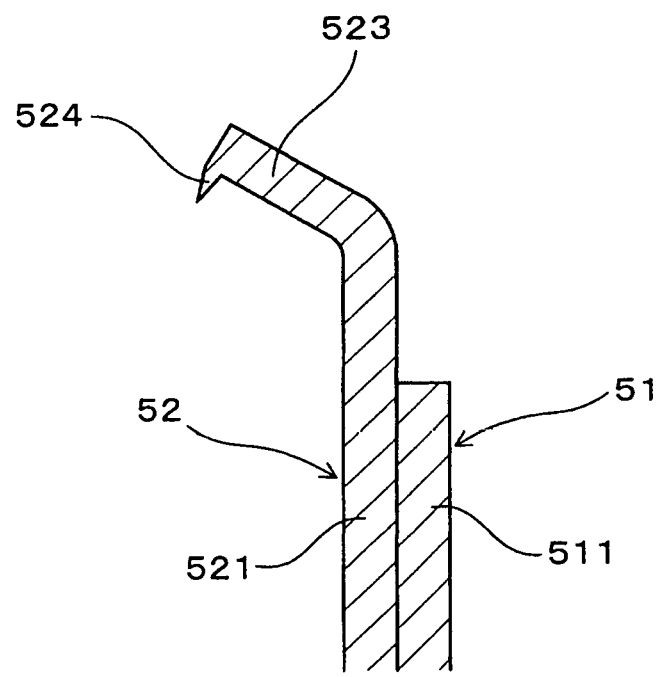
FIG. 8 is an explanatory enlarged sectional view which illustrates around a large-diameter portion formed on an outer cover.

Instead of the large-diameter portion 513 of the inner cover 51, the outer cover 51, as illustrated in FIG. 8, may has the large-diameter portion 523 formed thereon. In this case, the large-diameter portion 523 of the outer cover 52 is equipped with the convex portion 524. The gas sensor 1 is designed to have a double structure made up of the inner cover 51 and the outer cover 52, but may alternatively be made by a single cover. In this case, the single cover may have the large-diameter portion 513 formed on a rear end portion thereof.

The inner cover 51 and the outer cover 52 may have, as illustrated in FIGS. 9(a) to 9(c), large-diameter portions 513A and 523A which are laid to overlap each other. The large-diameter portions 513A and 523A may have, as illustrated in FIG. 9(a), top ends aligned with each other. The top end of the large-diameter portion 523A may alternatively, as illustrated in FIG. 9(b), protrude outwardly from that of the large-diameter portion 513A. The top end of the large-diameter portion 513A may alternatively, as illustrated in FIG. 9(c), protrude outwardly from that of the large-diameter portion 523A.

The invention claimed is:

1. A gas sensor comprising:
   a tubular housing;
   a device body which is inserted into an inner peripheral hole of the housing, the device body being a gas sensing device or a member into which the gas sensing device is inserted; and
   a cover which covers a portion of the gas sensing device and is held between the inner peripheral hole of the housing and the device body,
   wherein the inner peripheral hole of the housing includes a front end side hole portion, a rear end side hole portion, and a step portion, the front end side hole portion being located on a front end side of the device body, the rear end side hole portion being located closer to a rear end side than the front end side hole portion is and having a diameter greater than that of the front end side hole portion, the step portion being formed in a vertical or slant shape at a boundary between the rear end side hole portion and the front end side hole portion,
   in that the cover includes a tubular portion inserted into the front end side hole portion and a large-diameter portion which has a diameter greater than the tubular portion and faces the step portion,
   in that the device body has a flange which protrudes from an outer circumference thereof and holds the large-diameter portion between itself and the step portion,
   in that at least one of surfaces of the step portion and the large-diameter portion which face each other has a convex portion protruding toward the other surface, and
   the large-diameter portion directly contacts the flange of the device body and the step portion of the housing.

2. A gas sensor as set forth in claim 1, wherein the large-diameter portion is formed on an end portion of the tubular portion in a slant shape whose diameter increases toward a rear end side of the tubular portion, in that the step portion is formed in a slant shape whose diameter increases toward the rear end side, and in that the convex portion is formed on at least one of a surface of a front end portion of the step portion and a surface of a rear end portion of the large-diameter portion.

3. A gas sensor as set forth in claim 2, wherein the convex portion is formed to protrude from a surface of the large-diameter portion of the cover.

4. A gas sensor as set forth in claim 1, wherein the convex portion protrudes from a surface of the step portion of the housing.

5. A gas sensor as set forth in claim 1, wherein the convex portion is implemented by a plurality of protrusions formed on at least one of the step portion and the large-diameter portion.

6. A gas sensor as set forth in claim 3, wherein:
   the convex portion formed to protrude from the surface of the large-diameter portion of the cover is a burr; and
   the burr is inserted into a recess defined in the step portion of the housing.

7. A gas sensor as set forth in claim 4, wherein:
   the convex portion that protrudes from the surface of the step portion of the housing is a pointed head; and
   the pointed head is inserted into a recess defined in the large-diameter portion of the cover.

8. A gas sensor as set forth in claim 7, wherein:
the pointed head points in a direction that is parallel to a longitudinal axis of the gas sensing device.

\* \* \* \* \*